US012649017B2

(12) United States Patent
Sevinc et al.

(10) Patent No.: US 12,649,017 B2
(45) Date of Patent: Jun. 9, 2026

(54) MULTILAYER MEDICAL TUBING WITH LOW SORBABILITY

(71) Applicant: CareFusion 303, Inc., San Diego, CA (US)

(72) Inventors: Zehra Sevinc, San Diego, CA (US); Mark Doane, San Diego, CA (US); Lawrence Trainer, San Diego, CA (US); Wantjinarjo Suwito, San Diego, CA (US); Anthony Guevara, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 17/520,220

(22) Filed: Nov. 5, 2021

(65) Prior Publication Data

US 2022/0143273 A1      May 12, 2022

Related U.S. Application Data

(60) Provisional application No. 63/111,538, filed on Nov. 9, 2020.

(51) Int. Cl.
*A61L 29/04* (2006.01)
*A61L 29/06* (2006.01)
(Continued)

(52) U.S. Cl.
CPC ............. *A61L 29/041* (2013.01); *A61L 29/06* (2013.01); *B29C 48/0015* (2019.02);
(Continued)

(58) Field of Classification Search
None
See application file for complete search history.

(56) References Cited

U.S. PATENT DOCUMENTS 4,606,558 A      8/1986   Davidson
4,705,511 A      11/1987   Kocak
(Continued)

FOREIGN PATENT DOCUMENTS

CN            1639495 A       7/2005
CN          101678659 A       3/2010
(Continued)

OTHER PUBLICATIONS

International Search Report and Written Opinion for Application No. PCT/US2021/057785, dated Feb. 11, 2022, 14 pages.
(Continued)

*Primary Examiner* — Thomas J Kessler
(74) *Attorney, Agent, or Firm* — Maschoff Brennan

(57) ABSTRACT
Medical tube can have a continuous inner layer having a continuous outer layer thereon, in which the inner layer includes a polyolefin such as a polyethylene or polypropylene or a functionalized polyolefin. The outer layer can include a thermoplastic polymer such as one or more of, or a blend including, a thermoplastic polyurethane (TPU), a thermoplastic olefin (TPO), a thermoplastic elastomer (TPE), a styrene-containing thermoplastic elastomer (S-TPE), a polyolefin elastomer (POE), a styrenic blocking copolymer (SBC). Advantageously, the outer layer and/or the inner layer do not include polyvinyl chloride. Such tubing can be used as medical device such as with infusion sets.

20 Claims, 4 Drawing Sheets

(51) Int. Cl.

| | |
|---|---|
| *B29C 48/00* | (2019.01) |
| *B29C 48/22* | (2019.01) |
| *B29K 23/00* | (2006.01) |
| *B29K 75/00* | (2006.01) |

(52) U.S. Cl.
CPC .......... *B29C 48/22* (2019.02); *B29K 2023/06* (2013.01); *B29K 2023/12* (2013.01); *B29K 2075/00* (2013.01); *B32B 2597/00* (2013.01)

(56) References Cited

U.S. PATENT DOCUMENTS

| | | | | |
|---|---|---|---|---|
| 5,281,670 | A * | 1/1994 | Lee | C08L 23/20 |
| | | | | 525/207 |
| 5,681,627 | A * | 10/1997 | Mueller | B32B 27/40 |
| | | | | 604/408 |
| 5,721,315 | A * | 2/1998 | Evans | C08F 8/32 |
| | | | | 525/379 |
| 5,741,452 | A * | 4/1998 | Ryan | B29C 55/22 |
| | | | | 264/235.6 |
| 5,803,130 | A | 9/1998 | Robben et al. | |
| 5,866,257 | A | 2/1999 | Schledjewski et al. | |
| 5,932,307 | A * | 8/1999 | Ryan | A61L 29/041 |
| | | | | 604/408 |
| 7,264,858 | B2 * | 9/2007 | Belliveau | C08G 18/758 |
| | | | | 428/36.91 |
| 7,641,753 | B2 | 1/2010 | Gao et al. | |
| 8,178,647 | B2 | 5/2012 | Hawkins et al. | |
| 8,735,491 | B2 | 5/2014 | Kim et al. | |
| 9,625,061 | B2 | 4/2017 | Liu et al. | |
| 10,646,704 | B2 | 5/2020 | Bourgeois et al. | |
| 2007/0051418 | A1 | 3/2007 | Rowles et al. | |
| 2009/0087606 | A1 * | 4/2009 | Julien | B32B 27/304 |
| | | | | 428/36.6 |
| 2010/0143651 | A1 * | 6/2010 | Silvis | C08L 23/0815 |
| | | | | 36/98 |
| 2012/0048380 | A1 | 3/2012 | Thomas et al. | |
| 2013/0186469 | A1 | 7/2013 | Bourgeois | |
| 2013/0190714 | A1 | 7/2013 | Bourgeois et al. | |
| 2015/0247592 | A1 | 9/2015 | Bourgeois et al. | |
| 2017/0226272 | A1 * | 8/2017 | Cozzens | C08G 18/722 |
| 2018/0117295 | A1 | 5/2018 | Wolkenstoerfer et al. | |
| 2019/0091962 | A1 | 3/2019 | Kurumiya et al. | |
| 2019/0224384 | A1 * | 7/2019 | Lundahl | A61L 29/14 |
| 2019/0309157 | A1 * | 10/2019 | Karube | B29C 48/30 |
| 2021/0244931 | A1 * | 8/2021 | Doane | B29C 48/09 |

FOREIGN PATENT DOCUMENTS

| | | | | | | |
|---|---|---|---|---|---|---|
| CN | 104583660 | A | | 4/2015 | | |
| CN | 106421937 | A | | 2/2017 | | |
| CN | 109171617 | A | | 1/2019 | | |
| EP | 0174206 | A2 | | 3/1986 | | |
| EP | 3283159 | B1 | | 5/2019 | | |
| JP | H0833705 | A | | 2/1996 | | |
| JP | 2001269403 | A | | 10/2001 | | |
| JP | 2003102827 | A | | 4/2003 | | |
| JP | 2005318949 | A | | 11/2005 | | |
| JP | 2008132659 | A | | 6/2008 | | |
| JP | 2010088894 | A | | 4/2010 | | |
| JP | 2010514852 | A | | 5/2010 | | |
| JP | 2013116320 | A | | 6/2013 | | |
| JP | 2015509870 | A | | 4/2015 | | |
| JP | 2018000746 | A | * | 1/2018 | | |
| KR | 1020130052683 | A | | 5/2013 | | |
| WO | WO-9504652 | A1 | | 2/1995 | | |
| WO | WO-0076564 | A1 | * | 12/2000 | .......... | A61L 29/126 |
| WO | WO-03064909 | A1 | | 8/2003 | | |
| WO | 2008079784 | A2 | | 7/2008 | | |
| WO | WO-2014018877 | A1 | | 1/2014 | | |
| WO | WO-2014028136 | A1 | | 2/2014 | | |
| WO | WO-2014028700 | A1 | | 2/2014 | | |
| WO | WO-2021076990 | A1 | | 4/2021 | | |

OTHER PUBLICATIONS

International Preliminary Report on Patentability from the International Preliminary Examining Authority for International Application No. PCT/US2021/057785, dated Oct. 17, 2022, 14 pages.

European Office Action for Application No. 21836258.0, dated May 28, 2024, 5 pages.

Brazilian Office Action for Application No. BR112023007800-8, published Sep. 23, 2025, 5 pages including translation.

Chinese Office Action for Application No. 202111320136.7, dated Aug. 7, 2025, 16 pages including translation.

Japanese Office Action for Application No. 2023-526055, dated Jul. 16, 2025, 6 pages including translation.

Full Text Machine Translation of previously cited Japanese Publication No. JP2013116320-A, published Jun. 13, 2013, 16 pages.

Chinese Office Action for Application No. 202111320136.7, dated Jan. 1, 2026, 11 pages including translation.

Indian Office Action for Application No. 202317033781, dated Feb. 5, 2026, 9 pages.

Japanese Office Action for Application No. 2023-526055, dated Jan. 27, 2026, 9 pages including translation.

Chinese Notification to Grant for Application No. 202111320136.7, dated Apr. 2, 2026, 10 pages including translation.

* cited by examiner

22

24

20

MULTILAYER MEDICAL TUBING WITH LOW SORBABILITY

CROSS-REFERENCE TO RELATED APPLICATION

This application claims the benefit of U.S. Provisional Application No. 63/111,538 filed 9 Nov. 2020, the entire disclosure of which is hereby incorporated by reference herein.

TECHNICAL FIELD

The present disclosure generally relates to tubing and, in particular, to flexible medical tubing having low absorption of medicinal fluids and components therein. Such tubing can be used for medical devices such as tubing for administration of medical fluid by infusion.

BACKGROUND

Plastic tubing is extensively used in the medical field, particularly for patient analysis and treatment procedures. However, different and sometimes incompatible demands are required for medical tubing. For example, medical tubing should be strong yet soft or pliable, resist kinks, resist reacting with the fluid and avoid injecting adverse chemicals into fluid transported there through. But many plastic materials that have such characteristics tend to be inflexible. In many applications, however, medical tubing is pinched or clamped or used with infusion pumps that move fluid through the tubing by compressing the tubing. Such uses require the tubing to be flexible, easy to pinch and rebound quickly. Soft tubing such as polyvinyl chloride with plasticizer have been used in infusion sets for many years. Unfortunately, plasticized polymeric materials such as plasticized polyvinyl chloride can be sticky and can lead to occlusion and tearing of the tubing.

Hence, a continuing need exists for medical tubing that can address differing demands of medical applications.

SUMMARY

Aspects of the subject technology relate to medical tubing comprising a continuous inner layer having a continuous outer layer thereon. Advantageously, the inner layer comprises a polyolefin and the outer layer comprises a polymeric material that is different from the inner layer such as a different thermoplastic polymer.

The polyolefin inner layer can comprise a polyethylene or polypropylene or a functionalized polyolefin or a combination thereof wherein the functionalized polyolefin can be selected from a maleic anhydride modified polyethylene, a maleic anhydride modified polypropylene, a maleic anhydride modified plastomer, an amine functionalized polyolefin, or a combination thereof. The outer layer can comprise a thermoplastic polymer such as one or more of, or a blend including, a thermoplastic polyurethane (TPU), a thermoplastic olefin (TPO), a thermoplastic elastomer (TPE), a styrene-containing thermoplastic elastomer (S-TPE), a polyolefin elastomer (POE), a styrenic blocking copolymer (SBC). Advantageously, the outer layer and/or the inner layer do not include polyvinyl chloride.

The subject technology also relates to a method of manufacturing medical tubing by coextruding a continuous inner layer having a continuous outer layer directly thereon, wherein the inner layer comprises a polyolefin and the outer layer comprises a thermoplastic polymeric material that is different from the inner layer. The method can further include extruding a tie layer between the continuous inner layer and continuous outer layer. The manufactured medical tubing can be formed transparent to visible light.

Embodiments of the foregoing medical tubing and methods include one or more of the following features individually or combined. In some embodiments, the medical tubing can further comprises a tie layer between the continuous inner layer and continuous outer layer. The tie layer can comprise a maleic anhydride modified polypropylene, a maleic anhydride modified polyethylene, an ethyl vinylacetate copolymer, or combinations thereof. Alternatively, the inner layer can directly contact the outer layer. Further, in other embodiments, the medical tubing can comprise an intermittent solvent bondable segment layer directly contacting the outer layer such as a thermoplastic polyurethane intermittent solvent bondable segment layer.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawing, which is included to provide further understanding and is incorporated in and constitute a part of this specification, illustrate disclosed embodiments and together with the description serve to explain the principles of the disclosed embodiments. In the drawings.

DETAILED DESCRIPTION

Figure 1:
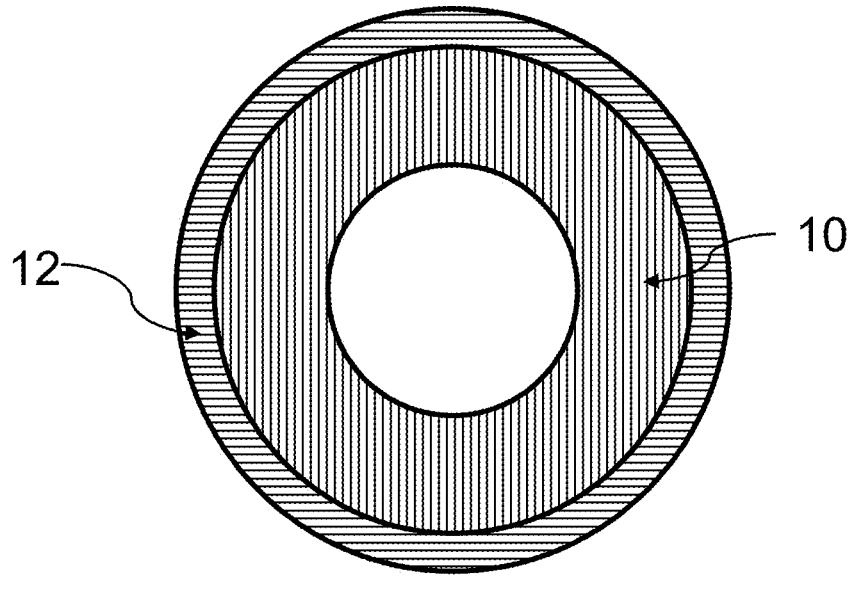
FIG. 1 illustrates an exemplary medical tube with a continuous inner and outer layer in accordance with aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to medical tubing that can accommodate differing property requirements. Advanced material formulations and architectures are needed for the medical tubing to overcome technical challenges arising from conflicting design requirements for such tubing. For example, medical tubing should be capable of bonding to joints and other components to connect the tubing such as by solvent bonding, bonding with adhesives or mechanical connections. Further medical tubing should simultaneously resist absorbing medicinal fluid and components therein with no changes to the tubing itself or any active pharmaceutical ingredient (API). That requires both an inert material for drug compatibility and a solvent responsive material for solvent bond-ability, which are typically conflicting requirements for a single material. Further there is a drive towards more environmentally friendly materials and to exclude polyvinyl chloride (PVC). Even though the tubing is expected to recover fast fully it also needs to be rigid to enable cutting processes for manufacturability.

Medical tubing of the present disclosure can be used as medical tubing for administration of medical fluid by infusion such as with intravenous assemblies, gravity containers and/or infusion pumps for the transport of intravenous fluid to a patient. An assembly of tubing, valves, fittings, and needles that connect a fluid container to a patient intravenously may be referred to as an "IV set". Infusion pumps are medical devices that may be used to administer intravenous (IV) fluids. Such assemblies, containers and pumps employ tubing bound to one or more medical connectors and tubing of the present disclosure is useful as such.

In some aspects, the subject technology relates to medical tubing comprising a continuous inner layer having a continuous outer layer thereon. Advantageously, the inner layer comprises a polyolefin which has low absorption characteristics such that the polyolefin inner layer resists absorbing medicinal fluid and/or components therein or affecting any active pharmaceutical ingredient (API) being transported through the tubing. In addition, the polyolefin inner layer resists changes to the tubing itself by the transport of medicinal fluid therethrough.

In some embodiments, the continuous inner layer can comprise a functionalized polyolefin such as a maleic anhydride modified polyethylene (e.g., a high density polyethylene HDPE or a low density polyethylene LDPE), a maleic anhydride modified polypropylene, maleic anhydride modified plastomer, or a combination thereof. Such functionalized polyolefins facilitate interlayer adhesion bonding between the inner and outer layers.

The outer layer can comprise a polymeric material different from the inner layer such that the outer surfaces of the tubing can have different properties from the inner layer materials. For example, the outer can comprise a thermoplastic polymer or a blend thereof such as, one or more or blend including, a thermoplastic polyurethane (TPU), a thermoplastic olefin (TPO), a thermoplastic elastomer (TPE), a styrene-containing thermoplastic elastomer (S-TPE), a polyolefin elastomer (POE), a styrenic blocking copolymer (SBC). The thermoplastic polymers useful as outer layers can further be blended with other polymeric components and/or additives. For example, thermoplastic polymers useful as outer layers can further be blended with adhesion promoters, such as acrylic based TPEs, or polar functionalized polyolefins, such as up to 15 wt % or more of the blend, tackifiers, and clarifying agents, such as up to 10 wt % of the blend. Many of the thermoplastic polymers have advantageous properties for the outer layer of medical tubing such as thermoplastic polyurethanes (TPU), which can be useful in solvent bonding the outer layer of the tubing. Alternatively, or in combination, many of the thermoplastic polymers advantageously improve flexibility of the tubing.

In some aspects of the medical tubing of the present disclosure, a tie layer can be included between the continuous inner layer and continuous outer layer.

Advantageously, the medical tubing of the present disclosure does not include polyvinyl chloride. That is, the outer layer and/or the inner layer and/or tie layer, if present, does not include polyvinyl chloride.

In some aspects, the medical tubing of the present disclosure can have a Shore A hardness of greater than about 85 or less than about 85. Hardness of Shore A greater than about 85 for medical tubing application is typically considered hard. Pump tubing typically employs softer tubing having a Shore A hardness of less than about 65, e.g., 55 or less.

The following medical tubing constructions and material formulations can meet many of the demands of an IV set and other demands of medical tubing.

TABLE 1

Solvent Bondable, Low Sorbing Polyolefin Lined TPU Medical Tube Construction.

| Outer Layer - Thermoplastic Polyurethane | Inner Layer - Functionalized Polyolefin |
|---|---|
| Tecoflex EG-85A or | Toyo-Tac M-100 (1) |
| Pellethane 2362-80A or | Exxelor PE1040 (2) |
| Ellastollan 1180A or | TecnoBond PE-LMP (3) |
| Tecothane TT1095A TPU | Exxelor VA1840 (4) |
| Tecoflex EG-85A or | Custom made amine functionalized |
| Pellethane 2362-80A or | polyolefin through reactive extrusion: |
| Ellastollan 1180A (5) or | choice of Functionalized Polyolefin 1, 2, |
| Tecothane TT1095A TPU (6) | 3, 4 above reacted with polyether amines |

(1) Exxelor PE1040 is a maleic anhydride modified HDPE
(2) TecnoBond PE-LMP is a maleic anhydride PE
(3) Toyo-Tac M-100 is a maleic anhydride PP
(4) VA1840 is a maleic anhydride modified plastomer
(5) Ellastollan 1180A is an ether based thermoplastic urethane
(6) Tecothane TT1095A TPU is a Shore A 95 TPU, which may satisfy different needs for small bore tubes.

As noted in Table 1, a continuous inner layer can comprise an amine functionalized polyolefin or maleic anhydride modified polyolefin. Such amine functionalized polyolefin can be prepared through reactive extrusion by combining and reacting a maleic anhydride modified polyolefin (e.g., choice of 1, 2, 3, 4 from Table 1 above) with a polyether amine. This formulation or maleic anhydride functionalized polyolefin allows increased compatibility of the polyolefin, a non-polar low surface energy material, with a more polar material group. Tube architecture in Table 1 requires good interlayer adhesion between a polar and non-polar material group, hence this customization should increase adhesion of the inner layer to the outer layer.

The two-layer polyolefin lined TPU medical tubing construction as provide in Table 1 offers several advantages, including: lack of a trilayer approach, increase in the processing line speed/line output compared with a trilayer, e.g., coextrusions run should be faster and less complicated than a trilayer. Standard cost is expected to be lower than trilayer, good adhesion of layers due to compatibilization via functionalization of the inner layer compared with poor adhesion of a non-modified polyolefin, low drug sorbing property as a result of the functionalized polyolefin inner layer.

Further in some embodiments, the continuous inner layer can be relatively thinner than the continuous outer layer which should encourage the tubing to have similar bulk properties of the TPU layer. In addition, ether based TPU layers provide better solvent bondability, and the choice of aliphatic backbone provides better color stability.

FIG. 1 illustrates an example of a two-layer polyolefin lined medical tube. Such a construction can be used with the polymeric materials listed in Table 1 above to provide a solvent bondable, low sorbing double layer polyolefin lined TPU medical tube. As shown, the two-layer medical tube includes as inner layer (10) and an outer layer (12) directly on the inner layer.

For use in applications including IV sets and/or infusion pumps, tubing of the present disclosure can have an inner diameter for flow of fluid therethrough ranging from about 1.5 mm to about 6 mm, e.g., from 2 mm to 4 mm. The overall sidewall thickness can range from about 0.2 mm to about 1 mm, such as from 0.4 mm to 0.6 mm. In some aspects of the present disclosure, the outer layer can comprise 10 to 90% of the side wall thickness, the inner layer can comprise 90 to 10% of the sidewall thickness. In an embodiment, the outer layer can have a thickness of about 0.01 mm to about 0.5 mm, e.g., from about 0.05 mm to about 0.2 mm, and the inner layer can have a thickness of about 0.1 mm to about 0.8 mm, e.g., from about 0.5 mm to about 0.5 mm.

Table 2 below is another example of a medical tubing construction that can be used according to the present disclosure.

TABLE 2

| Solvent Bondable Low Sorbing PE Lined TPU Tube with a Tie Layer | | |
| --- | --- | --- |
| Outer Layer - Thermoplastic Polyurethane | Tie Layer | Inner Layer Polyolefin |
| Tecoflex EG-85A or Pellethane 2362-80A or Ellastollan 1180A | TecnoBond PP-TLA (1) EC800AA (4) | 23R2A (2) EF612 MFI 2.5 (3) |
| | REPSOL HEALTHCARE ® HVA18G (5), see (6) | EF612 MFI 2.5 (3) |

(1) TecnoBond PP/TLA is a maleic anhydride modified random block PP copolymer
(2) Random PP copolymer extrusion grade
(3) LDPE
(4) Low-density polyethylene EC800 is a general-purpose low-density formulation used for extrusion coating applications.
(5) EVA copolymer
(6) Other alternatives include ReZilok Rx as a linear low-density polyethylene grafted with maleic anhydride.

As provided in Table 2, a medical tube can include a continuous inner layer, a continuous outer layer thereon and a tie layer between the continuous inner layer and continuous outer layer. As provided in Table 2, the inner layer can comprise a polyolefin such as a polypropylene or polyethylene (e.g., linear low-density polyethylene, LDPE). The outer layer can comprise a thermoplastic polyurethane (TPU), which can be useful in solvent bonding the outer layer of the tubing. The medical tubing can also include a tie layer between the continuous inner layer and continuous outer layer. Such a tie layer can comprise a functionalized polyolefin such as a maleic anhydride modified polypropylene, a maleic anhydride modified polyethylene, or other tie layer polymers such as an ethyl vinylacetate copolymer (EVA copolymer), or combinations thereof.

The three-layer polyolefin lined TPU medical tubing construction as provide in Table 2 offers several advantages, including: compatible backbone selection matching PP with PP based TPO or POP, matching PE with PE based TPO or POE enable compatibility without the need of a more expensive functionalized polymer, low drug sorbing property with inclusion of PP or PE based inner layer.

Further in some embodiments, the continuous inner layer can be relatively thinner than the continuous outer layer which should encourage the tubing to have similar bulk properties of the TPU layer. In addition, ether based TPU layers provide better solvent bondability, and the choice of aliphatic backbone provides better color stability.

Figure 2:
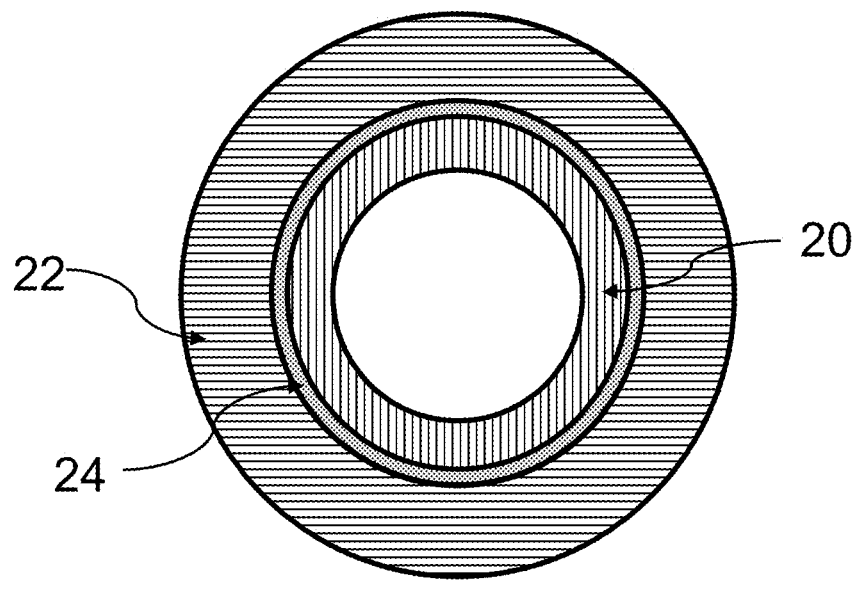
FIG. 2 illustrates another exemplary medical tube including a continuous inner layer, a continuous outer layer thereon and a tie layer between the continuous inner layer and continuous outer layer in accordance with aspects of the present disclosure.

FIG. 2 illustrates an example of a three-layer polyolefin lined medical tube. Such a construction can be used with the polymeric materials listed in Table 2 above to provide a solvent bondable, low sorbing polyolefin lined TPU medical tube with a tie layer. As shown, the three-layer medical tube includes an inner layer (20), an outer layer (22) and a tie layer (24) between and directly contacting inner layer (20) and outer layer (22).

For use in applications including IV sets and/or infusion pumps, tubing of the present discloser can have an inner diameter for flow of fluid therethrough ranging from about 1.5 mm to about 6 mm, e.g., from 2 mm to 4 mm. The overall sidewall thickness can range from about 0.2 mm to about 1 mm, such as from 0.4 mm to 0.6 mm. In some aspects of the present disclosure, the outer layer can comprise 10 to 90% of the side wall thickness, the inner layer can comprise 90 to 10% of the sidewall thickness. In an embodiment, the outer layer can have a thickness of about 0.1 mm to about 0.8 mm, e.g., from about 0.5 mm to about 0.5 mm, and the inner layer can have a thickness of about 0.01 mm to about 0.5 mm, e.g., from about 0.05 mm to about 0.2 mm.

Figure 3:
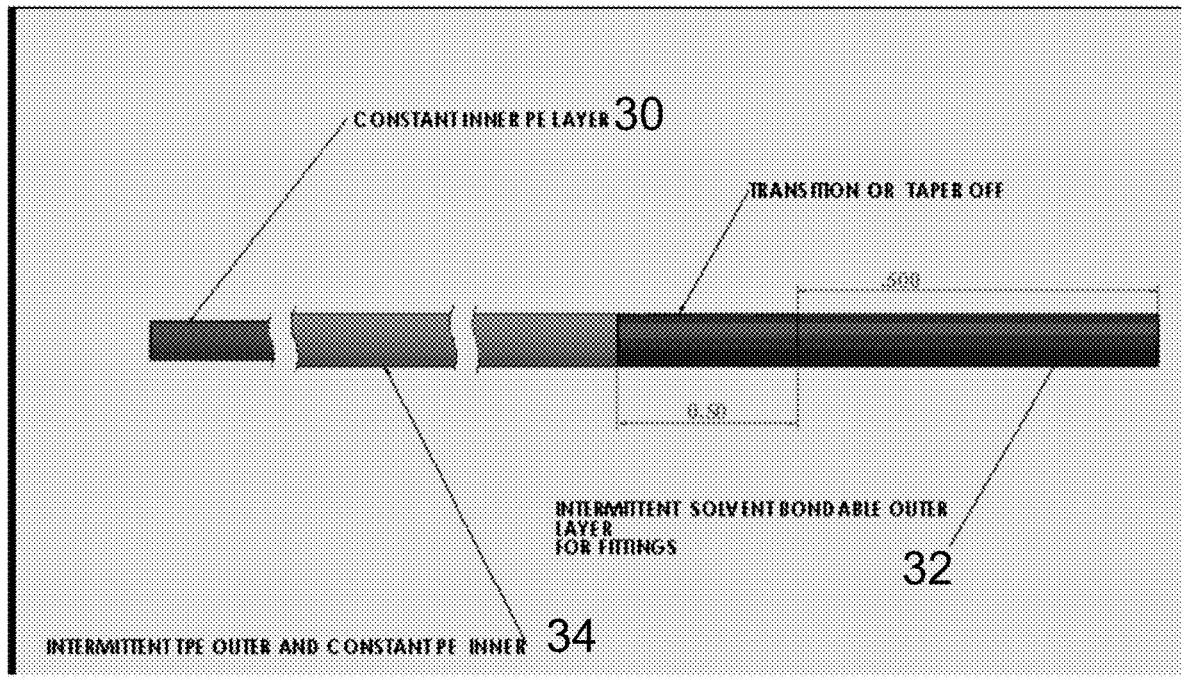
FIG. 3 illustrates another example of a two-layer polyolefin lined medical tube.

FIG. 3 illustrates another example of a two-layer polyolefin lined medical tube. Such a construction can be used to provide a solvent bondable, low sorbing polyolefin lined medical tube. As shown, the medical tube includes a continuous inner polyolefin layer (30) and a continuous outer layer (34). For this example, the medical tubing further includes an intermittent solvent bondable segment layer (32) directly contacting on outer layer 34. The intermittent solvent bondable segment layer can comprise a thermoplastic polyurethane such as a TPU with good bondability.

Table 3 below is another example of a medical tubing construction that can be used according to the present disclosure.

TABLE 3

| Low Sorbing PE lined TPO Two-Layer Tube. | |
| --- | --- |
| Outer Layer | Inner Layer |
| Engage 8003 (1) | LDPE, HDPE, other ethylene based polyolefins |
| Engage 8452 (2) | LDPE, HDPE, other ethylene based polyolefins |
| Versify 3300 (3) | Random PP copolymer, sterilization grade |
| Vistamaxx 3020 (4) | Random PP copolymer sterilization grade |

(1) Ethylene-octene polyolefin elastomer (POE)
(2) Ethylene-butene polyolefin elastomer (POE)
(3) POP
(4) Propylene elastomer, i-PP repeat units with random ethylene As provided in Table 3 above, a medical tube can include a continuous inner layer and a continuous outer layer directly thereon. The continuous inner layer can comprise a non-functionalized polyolefin such as polyethylene (e.g., a LDPE, HDPE) or polypropylene. The continuous outer layer can comprise a thermoplastic polymer such as an polyolefin elastomer (POE), e.g., an ethylene-octene polyolefin elastomer, ethylene-butene polyolefin elastomer, a polyolefin plastomer (POP), a propylene elastomer, as well as other thermoplastic polymers or blends thereof.

Many thermoplastic polymers including thermoplastic elastomers (TPE) and thermoplastic olefins useful for the outer layer of medical tubing of the present disclosure can be compounded with polyolefins for cost optimization, increased crystallinity, increased mechanical strength, increased working range, i.e., environmental stability and shelf life, and increased material compatibility, i.e., interlayer adhesion to the inner layer. Below are a few different customization that can overcome certain deficiencies of thermoplastic polymers from s-TPE and TPOs.

Custom made styrenic blocking copolymer (SBC) compounds: SBC grades are useful due to their flexibility as well as solvent response, i.e., bondability. However, some of our experiments indicate inferior kink resistance than other polymer types within the styrenics TPEs. Moreover, certain SBC grades lack the high temperature resistance as observed through low softening points. Similarly, POP and POE grades such as Engage reactor made TPOs lack the high temperature resistance as observed through low softening points. Tables 4-5 provides examples of thermoplastic polymer blends that can be used as a continuous outer layer of medical tubing according to the present disclosure.

SBC blend with random PP copolymer: An SBC blend with random PP copolymer will create a solvent bondable kink resistant material for tubing as-is or for solvent bondable layering. The blend ratios may vary from 5 to 95% of olefinic component (ethylene or propylene based) addition as to be further refined based on transparency requirement. These blends may also contain adhesion promoters such as acrylic based TPEs, or polar functionalized polyolefins up to 15 wt % (of the blend). Addition of tackifiers and clarifying agents, and polymer processing aids up to 10 wt % (of the blend) is typical for these types of compound when needed to modify the melt flow rheology and transparency of the tubing. Various processing variables can impact the transparency of the tubing as well as its mechanical properties.

TPO blend with random PP copolymer, polyolefins or temperature resistant TPOs such as Olefinic Block copolymers. The blend ratios may vary from 5 to 95% of olefinic component (ethylene or propylene based) which can be adjusted based on transparency requirement. These blends may also contain adhesion promoters such as acrylic based TPEs, or polar functionalized polyolefins up to 15 wt % of the blend. Addition of tackifiers and clarifying agents and polymer processing aids up to 10 wt % (of the blend) is typical for these types of compound when needed to modify the melt flow rheology and transparency of the tubing. Various processing variables can impact the transparency of the tubing as well as its mechanical properties.

TABLE 4

Examples of custom TPEs blends

| Function | Compound A | Compound B | Compound C |
|---|---|---|---|
| Elastomeric for flexibility, clarity | Engage 8003 | Engage 7256 | Engage 8452 |
| High Temperature Stability, Drug Compatibility (Low Sorbing of most grades), Cost Optimizer (Most Grades) | Ethylene based Polyolefin, LDPE, HDPE or alike | Ethylene based Polyolefin, LDPE, HDPE or alike | Ethylene based Polyolefin, LDPE, HDPE or alike |
| Adhesion, Rheology Modifiers | Acrylic based TPEs, Polar functionalized polyolefins, Tackifiers | Acrylic based TPEs, Polar functionalized polyolefins, Tackifiers | Acrylic based TPEs, Polar functionalized polyolefins, Tackifiers |
| Clarity Adjustment | Clarifying or Nucleating Agents, polymer processing aids, if needed | Clarifying or Nucleating Agents, polymer processing aids, if needed | Clarifying or Nucleating Agentspolymer processing aids, , if needed, |

TABLE 5

Additional examples of custom TPEs blends

| Function | Compound D | Compound E | Compound F |
|---|---|---|---|
| Elastomeric for flexibility, clarity | Engage 8003, POE | Infuse 9010 olefinic block copolymer (OBC) | Ineos 4G80 SBC |
| High Temperature Stability, Drug Compatibility (Low Sorbing of most grades), Cost Optimizer (Most Grades) | Infuse 9010, OBC | Random PP copolymer | Random PP copolymer |

TABLE 5-continued

| | Additional examples of custom TPEs blends | | |
| --- | --- | --- | --- |
| Function | Compound D | Compound E | Compound F |
| Adhesion, Rheology Modifiers | Acrylic based TPEs, Polar functionalized polyolefins, Tackifiers | Acrylic based TPEs, Polar functionalized polyolefins, Tackifiers | Acrylic based TPEs, Polar functionalized polyolefins, Tackifiers |
| Clarity Adjustment | Clarifying or Nucleating Agents, polymer processing aids, if needed | Clarifying or Nucleating Agents, polymer processing aids, if needed | Clarifying or Nucleating Agents, polymer processing aids, if needed |

Infuse 9010 olefinic block copolymer (OBC)
Engage 8003, Engage 7256, and Engage 8452 Polyolefin elastomer
Ineos 4G80 Styrene butadiene block copolymer A two-layer polyolefin lined thermoplastic polymer medical tubing construction, such as provide in Table 3, offers several advantages, including: lack of a trilayer approach, increase in the processing cycle time compared with a trilayer, e.g., coextrusions run should be faster and less complicated than a trilayer. cost is expected to be lower than trilayer, good adhesion of layers due to compatibilization with the inner layer, low drug sorbing property with inclusion of non-functionalized polyolefin inner layer.

The medical tubing of the present disclosure can be manufactured by extrusions. For example, medical tubing according to the present disclosure can be coextruded as a continuous inner layer having a continuous outer layer thereon, in which the inner layer comprises a polyolefin and the outer layer comprises a polymeric material that is different from the inner layer. It is preferable to make medical tubing that is clear, e.g., transparent to visible light. Extruding clear tubing has a set of challenges; the processing variables below can make a difference between transparent vs hazy tubing. Clarity is impacted by die temperatures, tooling design, and parison ventilation.

Die Temperatures: (a) Die temperatures will have an effect on the transparency of the tubing through its interaction with the surface finish of the tubing. Lowering the die temperatures near the end of the die will cause the outermost layer (the surface) of the tubing to "stick" to the tooling as its extruded. The sticking will cause a differential in velocity of the polymer melt from the inside to the outside, and will cause the surface to have micro deformations ("rips") on the surface. These rips cause the tubing to have an opaque or "frosted" appearance. (b) Conversely, increasing the die temperatures will serve to make the tubing more transparent by reducing the differential in polymer melt velocity from the inside to the outside, causing less micro deformations to appear on the surface.

Tooling Design: (a) Extrusion tooling can have a similar effect on surface finish as die temperatures does. By lowering the friction between the tooling material and the polymer melt, the polymer melt velocity would be more consistent throughout the parison. This reduction in friction is achieved through applying a finishing or coating process to the tooling.

Parison Ventilation: (a) One last process parameter that may have an effect on tubing transparency would be the placement of the parison vent. The purpose of the vent is to ventilate any fumes from the parison as it is extruded, and it is usually placed directly above the parison. A vent with a large opening can be placed farther away from the parison to catch any fumes, but a small snake type vent would have to be placed within inches of the parison. If the vent is placed too close to the parison, the parison would be affected by the suction of the air, and this would alter the surface finish of the tubing, potentially creating an opaque/frosted finish. (b) This is similar to a frosting extrusion process, where chilled air is blown onto the parison directly as it is extruded.

Figure 4:
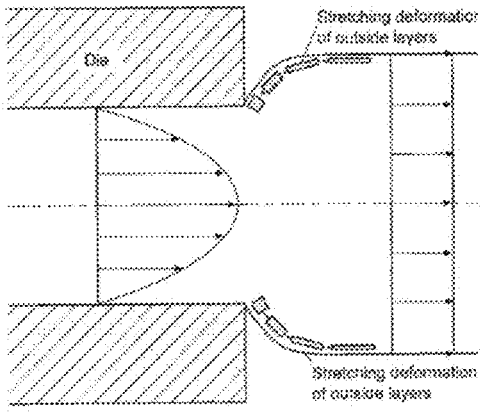
FIG. 4 illustrates how certain variables affect extrusion of medical tubing.
Figure 5:
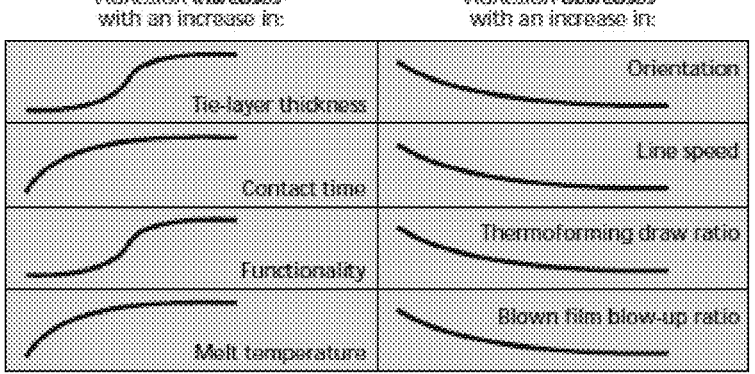
FIG. 5 shows the effects of adhesion strength by adjusting certain variables during extrusion.

FIG. 4 illustrates how items 1 and 2 below can be affected during extrusion and FIG. 5 shows the effects of adhesion strength by adjusting certain variables during extrusion.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. Medical tubing comprising a continuous inner layer having a continuous outer layer thereon and an intermittent solvent bondable segment layer directly contacting the continuous outer layer, wherein the intermittent solvent bondable segment layer is included for only a portion of the length of the medical tubing and the intermittent solvent bondable segment layer is configured to bond the medical tubing to a fitting, wherein the inner layer is formed of a functionalized polyolefin and the outer layer comprises a thermoplastic polymer, wherein material of the continuous inner layer is different than material of the continuous outer layer, wherein the functionalized polyolefin comprises an amine functionalized polyolefin combined with one or more of a maleic anhydride modified polyethylene, a maleic anhydride modified polypropylene, or a maleic anhydride modified plastomer, and wherein the medical tubing does not include polyvinyl chloride.

2. The medical tubing of claim 1, wherein the amine functionalized polyolefin is formed by reacting a polyether amine combined with a maleic anhydride modified polyolefin.

3. The medical tubing of claim 1, wherein the thermoplastic polymer comprises an ether based thermoplastic urethane.

4. The medical tubing of claim 1, wherein the inner layer directly contacts the outer layer.

5. The medical tubing of claim 1, further comprising a continuous second inner layer comprising a polyethylene or a polypropylene, wherein the functionalized polyolefin is a tie layer between the continuous second inner layer and the continuous outer layer.

6. The medical tubing of claim 5, wherein the continuous second inner layer is a linear low-density polyethylene.

7. The medical tubing of claim 1, wherein the outer layer comprises one or more of, or is a blend including, a thermoplastic olefin (TPO), a thermoplastic elastomer (TPE), a styrene-containing thermoplastic elastomer (S-TPE), a polyolefin elastomer (POE), and/or a styrenic block copolymer (SBC).

8. The medical tubing of claim 7, further comprising a continuous second inner layer comprising polyethylene or polypropylene.

9. The medical tubing of claim 1, wherein the thermoplastic polymer is a blend including one or more of an adhesion promotor and a clarifying agent.

10. The medical tubing of claim 1, wherein the medical tubing has a Shore A hardness of 55 or less.

11. The medical tubing of claim 1, wherein the intermittent solvent bondable segment layer comprises a thermoplastic polyurethane.

12. The medical tubing of claim 1, wherein the outer layer includes a tackifier.

13. Medical tubing consisting of a continuous inner layer having a continuous outer layer thereon, and an intermittent solvent bondable segment layer directly contacting on the outer layer, wherein the inner layer is formed of non-functionalized polyolefin and the outer layer comprises a thermoplastic polymer, wherein the outer layer and inner layer do not include polyvinyl chloride, and wherein the intermittent solvent bondable segment layer comprises a thermoplastic polyurethane, the intermittent solvent bondable segment layer is included for only a portion of the length of the medical tubing, and the intermittent solvent bondable segment layer is configured to bond the medical tubing to a fitting.

14. The medical tubing of claim 13, wherein the outer layer comprises a thermoplastic polymer blended with a random polypropylene copolymer.

15. The medical tubing of claim 13, wherein the outer layer includes a tackifier.

16. A method of manufacturing the medical tubing of claim 1, the method comprising coextruding the continuous inner layer having the continuous outer layer thereon.

17. The method of claim 16, wherein the medical tubing is transparent to visible light.

18. The method of claim 16, further comprising extruding a tie layer between the continuous inner layer and continuous outer layer.

19. The method of claim 16, further comprising extruding the intermittent solvent bondable segment layer directly contacting the continuous outer layer.

20. The method of claim 16, wherein the outer layer comprises a thermoplastic polyurethane.

\* \* \* \* \*